(12) United States Patent
Bornzin et al.

(10) Patent No.: US 8,391,980 B2
(45) Date of Patent: Mar. 5, 2013

(54) METHOD AND SYSTEM FOR IDENTIFYING A POTENTIAL LEAD FAILURE IN AN IMPLANTABLE MEDICAL DEVICE

(75) Inventors: Gene A. Bornzin, Simi Valley, CA (US); John W. Poore, South Pasadena, CA (US); Richard Williamson, Santa Monica, CA (US); Gabriel A. Mouchawar, Valencia, CA (US); Eric S. Fain, Menlo Park, CA (US)

(73) Assignee: Pacesetter, Inc., Sylmar, CA (US)

( * ) Notice: Subject to any disclaimer, the term of this patent is extended or adjusted under 35 U.S.C. 154(b) by 591 days.

(21) Appl. No.: 12/498,982

(22) Filed: Jul. 7, 2009

(65) Prior Publication Data

US 2011/0009918 A1 Jan. 13, 2011

(51) Int. Cl.
*A61N 1/00* (2006.01)
(52) U.S. Cl. .............. 607/27; 607/48; 607/116
(58) Field of Classification Search .......... 607/27, 607/48, 116
See application file for complete search history.

(56) References Cited

U.S. PATENT DOCUMENTS

| | | | |
|---|---|---|---|
| 5,558,098 | A | 9/1996 | Fain |
| 7,047,083 | B2 | 5/2006 | Gunderson et al. |
| 7,146,213 | B1 | 12/2006 | Levine |
| 7,158,829 | B1 | 1/2007 | Levine |
| 7,308,310 | B1 | 12/2007 | Levine et al. |
| 7,369,893 | B2 | 5/2008 | Gunderson |
| 2004/0064161 | A1 | 4/2004 | Gunderson et al. |
| 2005/0137636 | A1 | 6/2005 | Gunderson et al. |
| 2006/0247706 | A1 | 11/2006 | Germanson et al. |
| 2006/0264777 | A1* | 11/2006 | Drew .............................. 600/547 |
| 2006/0265024 | A1* | 11/2006 | Goetz et al. ...................... 607/48 |
| 2008/0221632 | A1 | 9/2008 | Bardy et al. |

FOREIGN PATENT DOCUMENTS

| | | |
|---|---|---|
| WO | 2004028617 A2 | 4/2004 |
| WO | 2004028617 A3 | 4/2004 |
| WO | 2005056109 A1 | 6/2005 |

OTHER PUBLICATIONS

Xu, Wenjie MD et al., "Veteran Survival Following Sprint Lead Implant," Supplement to Heart Rhythm Society. 2008;5(5S):S193 - Abstract PO2-92.

Thibault, Bernard MD et al., "Fidelis Versus Non-Fidelis RV Lead Fractures: Insights from the Ongoing Raft ICD/CRT Device Trialt," Supplement to Heart Rhythm Society. 2008;5(5S):S192 - Abstract PO2-91.

(Continued)

*Primary Examiner* — Nicole F Lavert

(57) ABSTRACT

A method for detecting potential failures by a lead of an implantable medical device is provided. The method includes sensing a first signal over a first channel between a first combination of electrodes on the lead and sensing a second signal from a second channel between a second combination of electrodes on the lead. The method determines whether at least one of the first and second signals is representative of a potential failure in the lead and identifies a failure and the electrode associated with the failure based on which of the first and second sensed signals is representative of the potential failure. Optionally, when the first and second sensed signals are both representative of the potential failure, the method further includes determining whether the first and second sensed signals are correlated with one another. When the first and second sensed signals are correlated, the method declares an electrode common to both of the first and second combinations to be associated with the failure.

13 Claims, 8 Drawing Sheets

OTHER PUBLICATIONS

Kallinen, Linda BS et al., "Does Patient Alert Warn of Impending Fracture in Sprint Fidelis ICD Lead?" Supplement to Heart Rhythm Society. 2008;5(5S):S81 - Abstract AB38-5.

Farwell, David J. MD et al., "Predictions of Sprint Fidelis Lead Fracture and Likelihood of Early Warning by Lead Ijmpedance Alerts," Supplement to Heart Rhythm Society. 2008;5(5S):S32 - Abstract AB16-2.

Ellenbogen, Kenneth A. MD, FHRS et al., "Algorithms for Early Identification of Sprint Fidelis ICD Lead Fractures," Supplement to Heart Rhythm Society. 2008;5(5S):S33 - Abstract AB16-3.

Swerdlow, Charles D. MD, FHRS et al., "Inappropriate Shocks Due to Spring Fidelis ICD Lead Fracture May Be Reduced by Programming More Intervals for Detection of Ventricular Fibrillation," Supplement to Heart Rhythm Society. 2008;5(5S):S33 - Abstract AB16-5.

* cited by examiner

FIG. 4-1

| | No fault operation | Failure Type 1 | Failure Type 2 | Failure Type 3 |
|---|---|---|---|---|
| Bipolar channel | *(waveform 430, 432, 434)* | *(waveform 438, 440)* | *(waveform 442)* | *(waveform 446)* |
| Integrated Bipolar channel | *(waveform 436, 432, 434)* | *(waveform 440)* | *(waveform 444)* | *(waveform 448)* |
| Result | Physiologic rate Good correlation | Not appropriate Different rates/no correlation | Not appropriate Different rates/no correlation | Not appropriate Good correlation |
| Do secondary test for Physiologic signal | If simultaneous high rate occurs; Perform a test for Physiologic rate, slew rate, and amplitude to check for failure 3 | Optional test: Integrated Bipolar not physiologic in rate, slew rate, or amplitude | Optional test: Bipolar not physiologic in rate, slew rate, or amplitude | May appear as a no fault operation but not physiologic in rate, slew rate, or amplitude and needs secondary checking for failure identification |
| Note system failure type | No fault operation | Declare Failure Type 1 | Declare Failure Type 2 | Declare Failure Type 3 |

FIG. 4-2

| | Clinical Alert | Mitigation | If high rate | Clinical response | Pacing |
|---|---|---|---|---|---|
| | None | None | Both channels agree – shock | No problem | No problem |
| | Alarm – total system failure – no protection | Replace lead as soon as possible if warranted | Shock if Bipolar channel shows high physiologic rate | Replace lead as soon as possible if warranted | Bipolar pacing continues |
| | Come in and Evaluate; Alert but can still operate | Ignore Bipolar channel | Shock if integrated Bipolar channel shows high physiologic rate | Recognize single fault and monitor patient and operate with Integrated Bipolar sensing | Switch to Integrated Bipolar pacing |
| | Come in and Evaluate; Alert but can still operate | Ignore both channels | Don't schock | Replace lead as soon as possible or change to Ring to Shocking coil sensing by programming (clinical judgment) | NO Pacing |

420 — Clinical Alert
422 — Mitigation
424 — If high rate
426 — Clinical response
428 — Pacing

METHOD AND SYSTEM FOR IDENTIFYING A POTENTIAL LEAD FAILURE IN AN IMPLANTABLE MEDICAL DEVICE

FIELD OF THE INVENTION

Embodiments of the present invention generally pertain to implantable medical devices and more particularly to methods and systems that identify potential lead failures in the devices and take corrective action based thereon.

BACKGROUND OF THE INVENTION

An implantable medical device (IMD) is implanted in a patient to monitor, among other things, electrical activity of a heart and to deliver appropriate electrical therapy, as required. Implantable medical devices include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm.

Electrodes coupled to leads are implanted in the heart to sense the electrical activity of the heart and to deliver electrical therapy to the heart. The electrodes communicate the electrical activity as cardiac signals to the IMD via the leads. The electrodes may be placed within the chambers of the heart and/or secured to the heart by partially inserting the electrodes into the heart. The cardiac signals sensed by the electrodes are used by the IMD to deliver appropriate pacing therapy and/or stimulation pulses, or "shocks" to the heart.

A lead failure occurs when an electrode fails. The electrodes may fail and no longer be capable of accurately sensing and communicating cardiac signals to the IMD. Known lead failures involve electrodes fracturing, breaking or becoming dislodged from the myocardium. Lead failures can result in increased noise in the cardiac signals communicated to the IMD. With respect to fractured electrodes, the noise may be caused by the fractured components of the electrode rapidly making and breaking contact with one another at the fracture site. This type of noise may be referred to as chatter noise.

Lead failures can result in an IMD applying unnecessary or incorrect pacing or stimulation pulses to the heart. For example, if chatter noise occurs at a sufficiently high rate, the IMD may misclassify the rate of the chatter noise as a tachycardia or fibrillation, such as ventricular tachycardia (VT) or ventricular fibrillation (VF). The IMD may then erroneously apply pacing or stimulation pulses to the heart. Such unnecessary pacing and stimulation pulses can cause significant discomfort to patients.

Systems have been proposed to detect lead failures based on certain parameters such as differences in R to R intervals, high impedance, impedance trends and slew rate. However, prior detection systems do not identify which individual electrode(s) is associated with a lead failure. Nor do prior detection systems offer robust solutions to mitigate failures in sensing electrodes.

Early detection of lead failures and the locations of the lead failures is desired. Early detection and notification of a lead failure may enable the patient's physician to reconfigure the IMD to avoid using the failed electrode. Alternatively, the physician may otherwise adjust treatment of a patient until the failed lead can be replaced. Known methods of detecting lead failures may not accurately detect a location of the lead failure. That is, while the method may be able to determine that a lead failure has occurred, the methods do not provide the patient's physician with a location of the failure, such as an identification of the electrode on the lead that has failed.

A need exists for a method and system that identifies a potential lead failure in an IMD and the location of the failure. As the application of stimulation and pacing pulses to a patient's heart largely depends on the accurate sensing of cardiac signals, detecting failed leads may avoid continued sensing using the failed leads. Additionally, earlier detection of failed leads may permit physicians to reconfigure operation of the IMD to avoid continued use of the failed leads until the leads can be replaced.

BRIEF SUMMARY OF THE INVENTION

In one embodiment, a method for detecting potential failures by a lead of an implantable medical device is provided. The method includes sensing a first signal over a first channel between a first combination of electrodes on the lead and sensing a second signal from a second channel between a second combination of electrodes on the lead. The method determines whether at least one of the first and second signals is representative of a potential failure in the lead and identifies a failure and the electrode associated with the failure based on which of the first and second sensed signals is representative of the potential failure. Optionally, when the first and second sensed signals are both representative of the potential failure, the method further includes determining whether the first and second sensed signals are correlated with one another. When the first and second sensed signals are correlated, the method declares an electrode common to both of the first and second combinations to be associated with the failure.

In another embodiment, an implantable medical device is provided. The device includes a lead, a channel selection module and a failure detection module. The lead includes electrodes configured to be positioned within a heart and capable of sensing cardiac signals to determine a first signal over a first channel between a first combination of the electrodes and a second signal over a second channel between a second combination of the electrodes. The channel selection module is configured to control which of the electrodes are included in the first and second combinations of electrodes. The failure detection module determines whether at least one of the first and second signals is representative of a potential failure in the lead. The failure detection module also identifies a failure and the electrode associated with the failure based on which of the first and second sensed signals is representative of the potential failure. Optionally, the failure detection module compares at least one of an amplitude, a rate and a slew rate of the first and second signals to a predetermined threshold representative of a physiologically acceptable limit for the corresponding one of the amplitude, rate and slew rate. The channel selection module may be configured to enable a different third channel to sense cardiac signals from a third combination of electrodes when a failure is identified by the failure detection module.

In another embodiment, a method is provided for detecting potential failures by an implantable medical lead. The method senses a first signal over a first channel between a first combination of electrodes on the lead. The method determines whether the first signal is representative of a potential failure in the lead, obtains a secondary indicator of heart condition and utilizes the secondary indicator to confirm an arrhythmia of the heart when the determining operation identifies the lead to include the potential failure. The secondary indicator may represent an impedance plethysmography measurement indicative of a stroke volume. The secondary indicator may represent a hemodynamic indicator from one of a pressure sensor located in a heart chamber, a heart sound sensor and a peak endocardial acceleration sensor. The secondary indicator may be obtained from a hemodynamic sensor, where the secondary indicator is tested after the determining operation identifies the potential failure based on the first signal, and the secondary indicator is analyzed before delivery of a therapy. The method may further comprise performing additional analysis of a heart, when the secondary indicator is representative of normal sinus rhythm, before delivering a therapy.

BRIEF DESCRIPTION OF THE DRAWINGS

The drawings illustrate generally, by way of example, but not by way of limitation, various embodiments discussed in the present document.

FIG. 4 includes a table displaying information and data relevant to various types of lead failures identified by the process shown in FIG. 3.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided for detecting potential failures of a lead in an implantable medical device. In one embodiment, the systems and methods described herein provide for the sensing of cardiac signals over different combinations of electrodes joined to a lead to identify an electrode associated with the lead failure.

Figure 1:
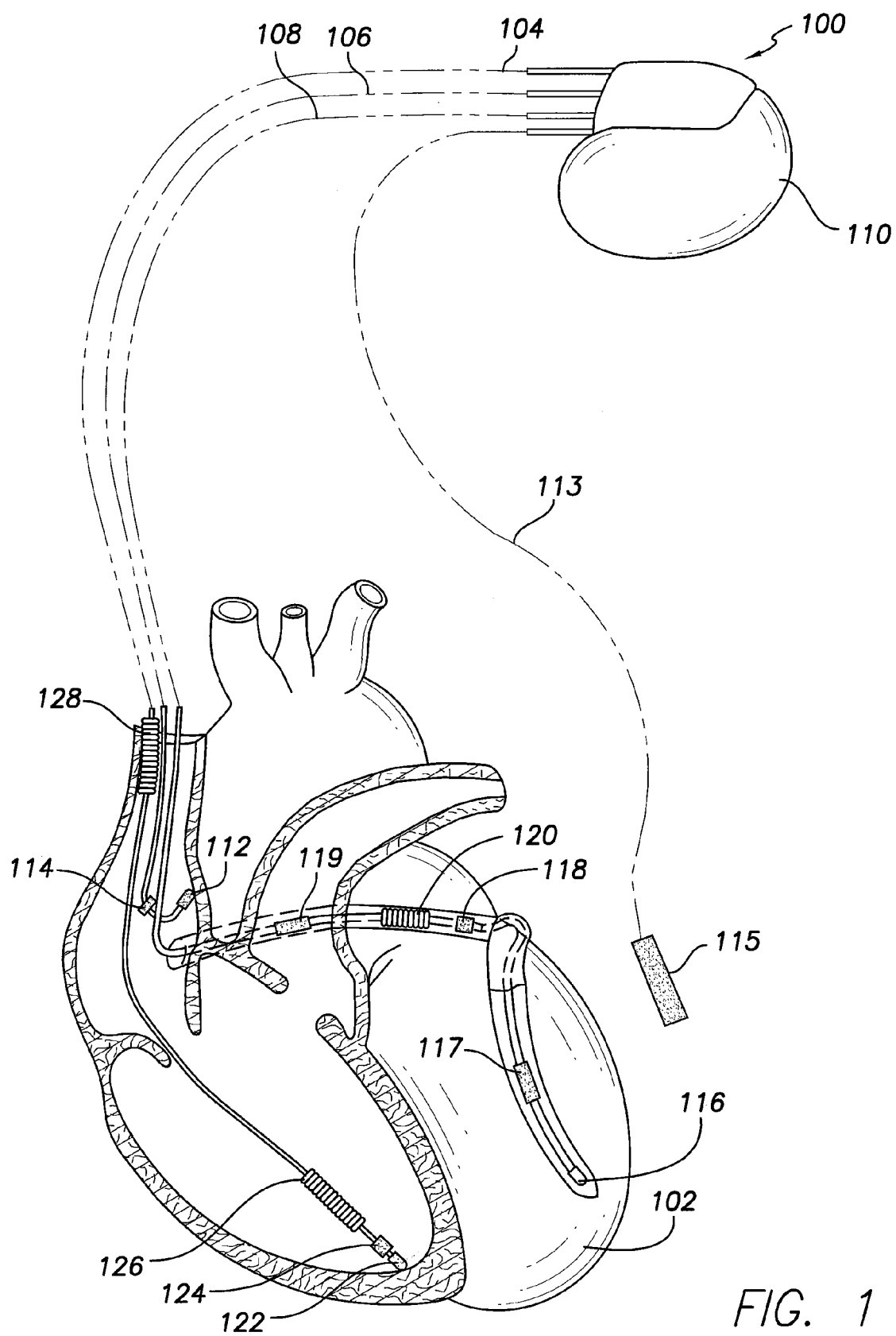
FIG. 1 illustrates an IMD coupled to a heart in accordance with one embodiment.

FIG. 1 illustrates an implantable medical device (IMD) 100 coupled to a heart 102 in accordance with one embodiment. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. Alternatively, the IMD 100 may be a triple- or quad-chamber stimulation device. Optionally, the IMD 100 may be a multi-site stimulation device capable of applying stimulation pulses to multiple sites within each of one or more chambers of the heart 102.

The IMD 100 includes a housing 110 that is joined to several leads 104, 106, 108. The leads 104, 106, 108 are located at various locations of the heart 102, such as an atrium, a ventricle, or both, to measure cardiac signals of the heart 102. The leads 104, 106, 108 include the right ventricular (RV) lead 104, the right atrial (RA) lead 106, and the coronary sinus lead 108. Several electrodes are provided on the leads 104, 106, 108. The housing 110 may be one of the electrodes and is often referred to as the "can", "case", or "case electrode." The RV lead 104 is coupled with an RV tip electrode 122, an RV ring electrode 124, and an RV coil electrode 126. The RV lead 104 may include a superior vena cava (SVC) coil electrode 128. The right atrial lead 106 includes an atrial tip electrode 112 and an atrial ring electrode 114. The coronary sinus lead 108 includes a left ventricular (LV) tip electrode 116, a left atrial (LA) ring electrode 118 and an LA coil electrode 120. Alternatively, the coronary sinus lead 108 may be a quadropole lead that includes several electrodes disposed within the left ventricle. Leads and electrodes other than those shown in FIG. 1 may be included in the IMD 100 and positioned in or proximate to the heart 102.

The IMD 100 senses cardiac signals over predetermined sensing channels on the leads 104-108. A sensing channel is formed by one, two or other combination of the electrodes 110-128. For example, the electrodes 110-128 associated with a channel may include two electrodes provided on the same lead 104-108 and/or located in the same chamber of the heart 102. Alternatively, a channel may include electrodes 110-128 provided on different leads 104-108 and/or located in different chambers of the heart 102. The electrodes used to sense cardiac signals for each channel are electrodes 112-128 primarily positioned inside the heart 102. Using electrodes 112-128 within the heart 102 to sense signals over the channels may reduce the risk of sensing myopotentials, which could affect the cardiac signals used to identify potential lead failures. In one embodiment, a first channel senses cardiac signals using the RV tip electrode 122 and the RV ring electrode 124. A second channel senses cardiac signals using the RV tip electrode 122 and the SVC coil electrode 128. The first channel may be referred to as a bipolar channel and the second channel may be referred to as an integrated bipolar channel. While the discussion herein is in connection with example bipolar and integrated bipolar channels, the channels may include a different combination of electrodes, including one or more of the housing 110, the LV tip electrode 116, the LA ring electrode 118, the LA coil electrode 120, and the like.

Optionally, one or more of the leads 104, 106, 108 may include a hemodynamic sensor 117 and/or 119 that obtains a secondary indicator of heart condition. Alternatively, or in addition, a hemodynamic sensor 115 may be provided on a separate lead 113 and located outside, but proximate to, the heart to monitor the heart condition. The sensors 115, 117 and 119 may represent one or more of an impedance plethysmography sensor to sense stroke volume, a pressure sensor to sense pressure in one or more chambers of the heart, a heart sound sensor to sense sounds produced by the heart and an endocardial sensor to sense a peak endocardial acceleration. The signals from sensors 115, 117 and 119 are representative of normal or abnormal sinus rhythm.

Figure 2:
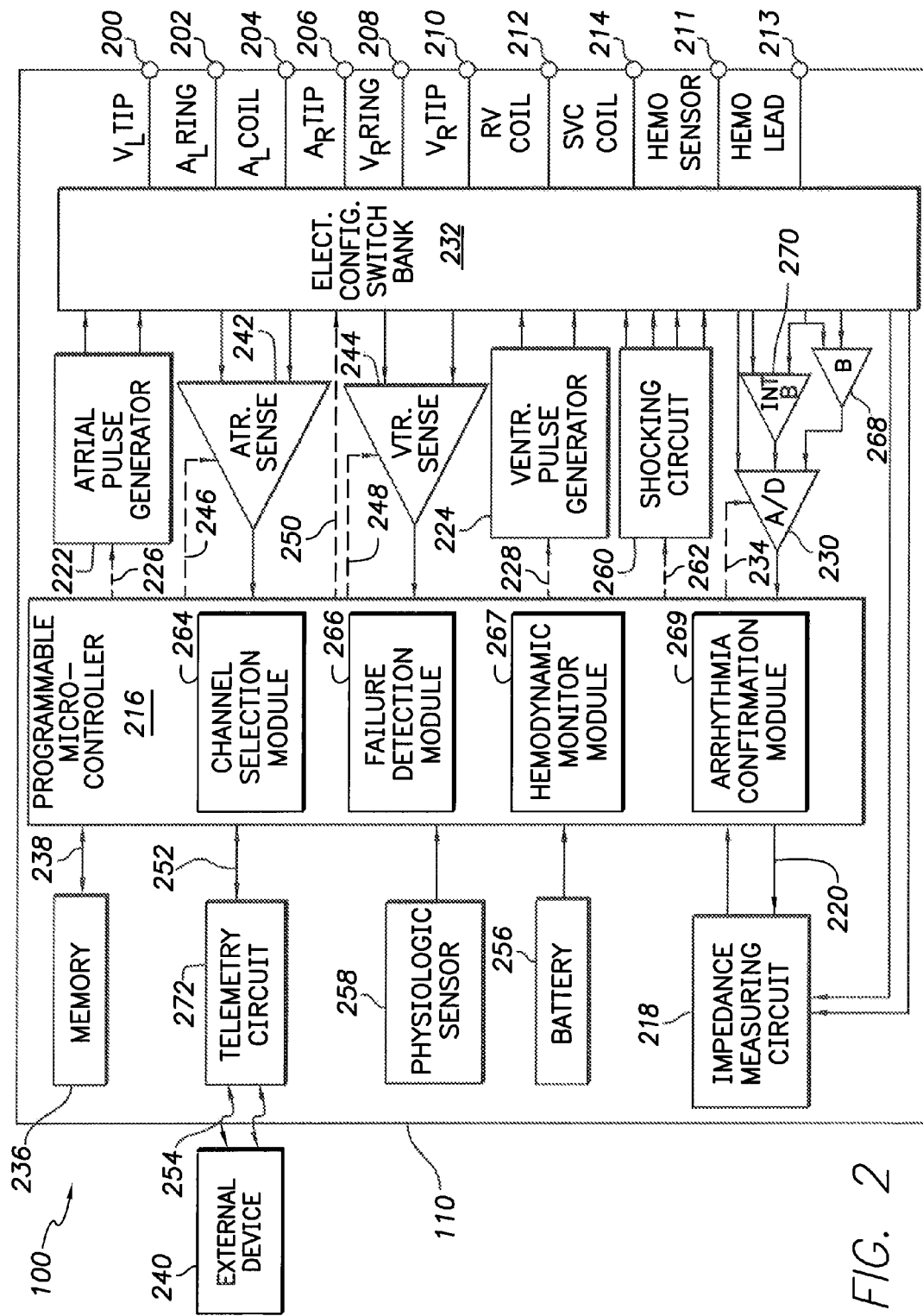
FIG. 2 illustrates a block diagram of exemplary internal components of the IMD shown in FIG. 1.

FIG. 2 illustrates a block diagram of exemplary internal components of the IMD 100. The housing 110 of the IMD 100 includes several inputs to receive signals measured or sensed by the electrodes 112-128 (shown in FIG. 1). The inputs may include one or more of an LV tip input (VL TIP) 200, an LA ring input (AL RING) 202, an LA coil input (AL COIL) 204, an RA tip input (AR TIP) 206, an RV ring input (VR RING) 208, an RV tip input (VR TIP) 210, an RV coil input 212 and an SVC coil input 214. The inputs may also include one or more hemodynamic sensor inputs 211 that are connected to sensors 117 and 119 on one or more of leads 104, 106, 108. One or more hemodynamic lead inputs 213 may be connected to one or more hemodynamic sensors 115 on a separate lead 113. As the names of the inputs 200-214 imply, the inputs 200-214 are electrically coupled with the corresponding electrodes and sensors 112-128 (shown in FIG. 1). For example, the LV tip input 200 may be connected with the LV tip electrode 116 (shown in FIG. 1); the LA ring input 202 may be connected with the LA ring electrode 118 (shown in FIG. 1); the LA coil input 204 may be connected with the LA coil electrode 120 (shown in FIG. 1); the RA tip input 206 may be connected with the RA tip electrode 112 (shown in FIG. 1); the RV ring input 208 may be connected with the RV ring electrode 124 (shown in FIG. 1); the RV tip input 210 may be connected with the RV tip electrode 122 (shown in FIG. 1); the RV coil input 212 may be connected with the RV coil electrode 126 (shown in FIG. 1); and the SVC coil input 214 may be connected with the SVC coil electrode 128 (shown in FIG. 1).

The IMD 100 includes a programmable microcontroller 216, which controls the operation of the IMD 100 based on sensed cardiac signals. The microcontroller 216 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. The microcontroller 216 receives, processes, and manages storage of digitized data from the various electrodes 112-128 (shown in FIG. 1).

The cardiac signals and hemodynamic signals sensed by the electrodes and sensors 112-128 are communicated through the inputs 200-214 to an electronically configured switch bank, or switch, 232. The switch 232 includes a plurality of switches for connecting the desired electrodes and switches 112-128 (shown in FIG. 1) and inputs 200-214 to the appropriate I/O circuits. The switch 232 closes and opens switches to provide electrically conductive paths between the circuitry of the IMD 100 and the inputs 200-214 in response to a control signal 250. The cardiac signals are then communicated to an analog-to-digital (A/D) data acquisition system 230, a bipolar sensing amplifier 268, or an integrated bipolar sensing amplifier 270. The hemodynamic signals are communicated through the A/D data acquisition system 230 to the microcontroller 216. The microcontroller 216 may sense cardiac signals over a first channel between the RV tip electrode 122 (shown in FIG. 1) and the RV ring electrode 124 (shown in FIG. 1) and over a second channel between the RV tip electrode 122 and the SVC coil electrode 128 (shown in FIG. 1). The first channel may also be referred to as the bipolar channel. The second channel may be referred to as the integrated bipolar channel. The amplifiers 268, 270 produce a difference between the input cardiac signals and output difference signals to the data acquisition system 230.

A control signal 234 from the microcontroller 216 determines when the data acquisition system 230 acquires signals, stores the signals in a memory 236 via a data/address bus 238, or transmits data to an external device 240 via a telemetry circuit 272. An atrial sensing circuit 242 and a ventricular sensing circuit 244 are selectively coupled to the leads 104-108 (shown in FIG. 1) and the electrodes 112-128 (shown in FIG. 1) through the switch 232 for sensing cardiac activity in the chambers of the heart 102 (shown in FIG. 1). Control signals 246, 248 from the microcontroller 216 direct output of the atrial and ventricular sensing circuits 242, 244.

The microcontroller 216 may include one or more modules and processors that examine the cardiac and hemodynamic signals to identify a potential failure in a lead 104-108 (shown in FIG. 1). The microcontroller 216 also may include modules and/or processors that enact or perform remedial responses or actions to mitigate the lead failure. A channel selection module 264 of the microcontroller 216 determines the sensing and therapy delivery channels. For example, the channel selection module 264 determines which combinations of the housing 110 and/or the electrodes 112-128 (shown in FIG. 1) are included in a particular sensing channel to sense cardiac signals associated with the particular sensing channel. The channel selection module 264 may vary which of the housing 110 and/or electrodes 112-128 are associated with a channel through the control signal 250 to the switch 232. Optionally, only the first channel or only the second channel may be used for sensing. The channel selection module 264 disables a channel when a lead failure involving one of the electrodes 112-128 associated with the channel is identified by the microcontroller 216. In order to mitigate a lead failure, the channel selection module 264 may disable sensing over a channel associated with the lead failure and enable a different channel to sense cardiac signals.

A failure detection module 266 determines whether a potential lead failure exists. For example and as described below, the failure detection module 266 may identify a potential lead failure based on cardiac signals sensed over the sensing channels. The failure detection module 266 identifies a lead failure and one or more electrodes 112-128 that are associated with the failure based on which of the signals from the sensing channel(s) are/is representative of the potential failure.

An impedance measuring circuit 218 measures electrical impedance characteristics between predetermined combinations of the housing 110 and/or the electrodes 112-128 (shown in FIG. 1). The impedance measuring circuit 218 is enabled by the microcontroller 216 via a control signal 220. The impedance measuring circuit 218 may measure a voltage potential at one or more electrodes 112-128 and/or a voltage potential difference between two or more electrodes 112-128. The electrical impedance measured may be utilized as a secondary indicator to confirm or reject a potential lead failure. An atrial pulse generator 222 and a ventricular pulse generator 224 each are configured to generate the pacing and/or non-pacing stimulation pulses to the atrial and ventricular chambers of the heart 102 (shown in FIG. 1), respectively. The pulse generators 222, 224 are controlled via corresponding control signals 226, 228 from the microcontroller 216 to trigger the stimulation pulses.

The memory 236 may be embodied in a computer-readable storage medium such as a ROM, RAM, flash memory, or other type of memory. The microcontroller 216 is coupled to the memory 236 by the data/address bus 238. The memory 236 may store programmable operating parameters and thresholds used by the microcontroller 216, as required, in order to customize operation of IMD 100 to suit the needs of a particular patient. The memory 236 may store data indicative of cardiac and hemodynamic signals sensed by the electrodes 112-128 (shown in FIG. 1). The operating parameters of the IMD 100 may be non-invasively programmed into the memory 236 through the telemetry circuit 272 in communication with the external device 240, such as a trans-telephonic transceiver or a diagnostic system analyzer. The telemetry circuit 272 is activated by the microcontroller 216 by a control signal 252. The telemetry circuit 272 allows cardiac signals, intra-cardiac electrograms, impedance measurements, status information, hemodynamic signals and other data relating to the operation of IMD 100 to be sent to the external device 240 through an established communication link 254.

In the case where IMD 100 is intended to operate as an ICD device, the IMD 100 detects the occurrence of a shift in one or more waveforms in sensed cardiac signals that indicates an arrhythmia, and automatically applies an appropriate electrical shock therapy to the heart 102 (shown in FIG. 1) aimed at terminating the detected arrhythmia. To this end, the microcontroller 216 further controls a shocking circuit 260 by way of a control signal 262. The shocking circuit 260 generates shocking pulses of low (up to 0.5 joules), moderate (0.5-10 joules) or high energy (11 to 40 joules). Such shocking pulses are applied to the heart 102 of the patient through at least two shocking electrodes, and as shown in this embodiment, selected from the LA coil electrode 120 (shown in FIG. 1), the RV coil electrode 126 (shown in FIG. 1), and/or the SVC coil electrode 128 (shown in FIG. 1).

A hemodynamic monitor module 267 collects and analyzes hemodynamic signals as a secondary indicator of the condition of the heart. When the module 267 is used, the IMD 100 may identify a potential arrhythmia based on cardiac signals while the hemodynamic signals indicate that the heart is in normal sinus rhythm. When the foregoing combination of contradictory indicators occurs, the IMD 100 may forego or delay delivery of the shock therapy for at least a supplemental analysis period of time. During the supplemental analysis time, an arrhythmia confirmation module 269 performs addition confirmation analysis of prior and/or new cardiac and/or hemodynamic signals. The addition analysis may utilize more robust arrhythmia detection algorithms (cardiac and/or hemodynamic based) that are not readily available for real-time continuous use. The addition analysis may review cardiac and/or hemodynamic signals from other chambers of the heart, collection and analysis of new cardiac and/or hemodynamic signals and the like. The IMD 100 may then deliver the therapy after the addition confirmation analysis, or abort any type of therapy, based on the results of the confirmation analysis.

A battery 256 provides operating power to the circuits of the IMD 100, including the microcontroller 216. The IMD 100 also includes a physiologic sensor 258 that may be used to adjust pacing stimulation rate according to the exercise state of the patient.

Figure 3A:
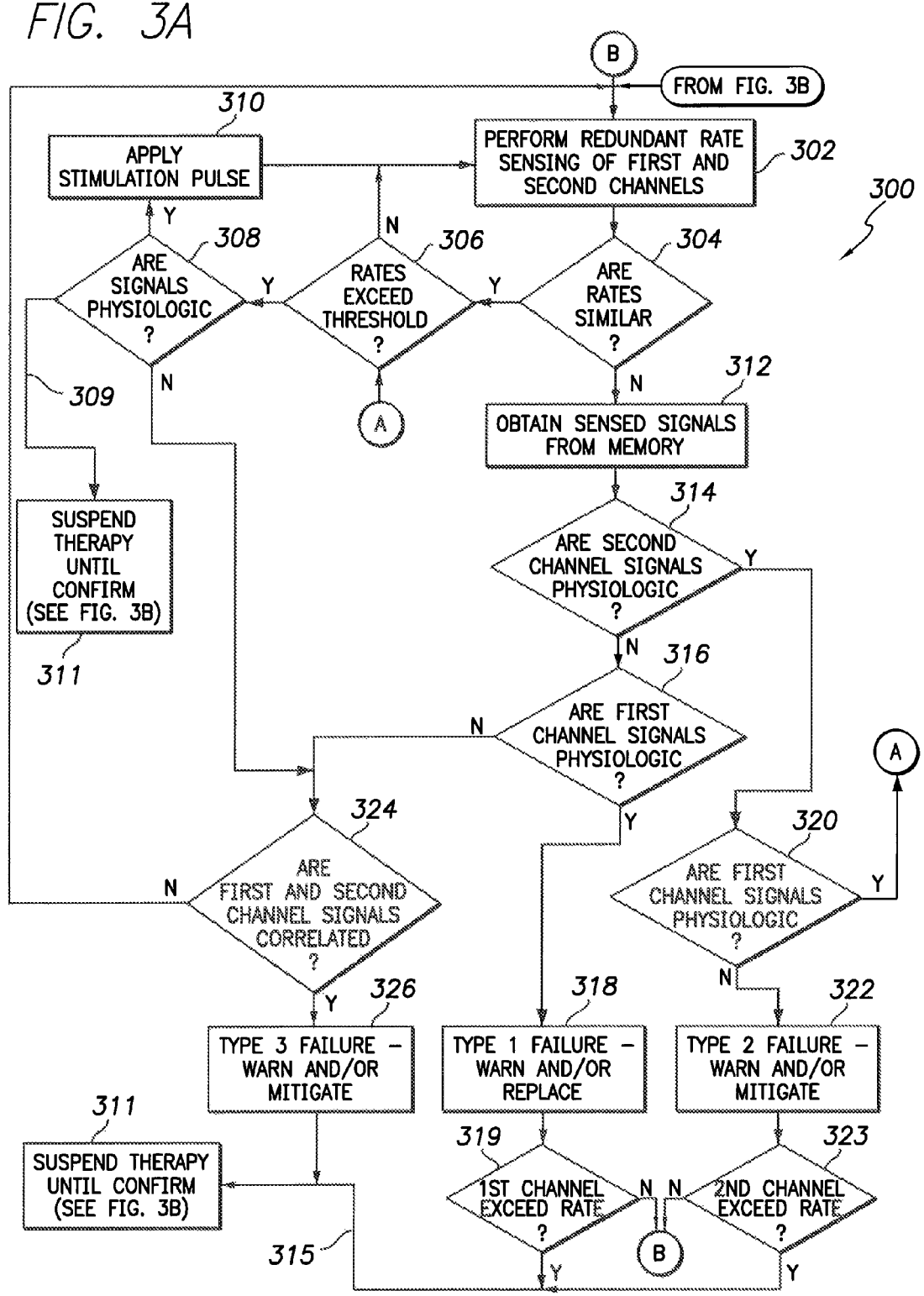
FIGS. 3A and 3B illustrates a process for detecting potential failures of a lead shown in FIG. 1 according to one embodiment.
Figure 3B:
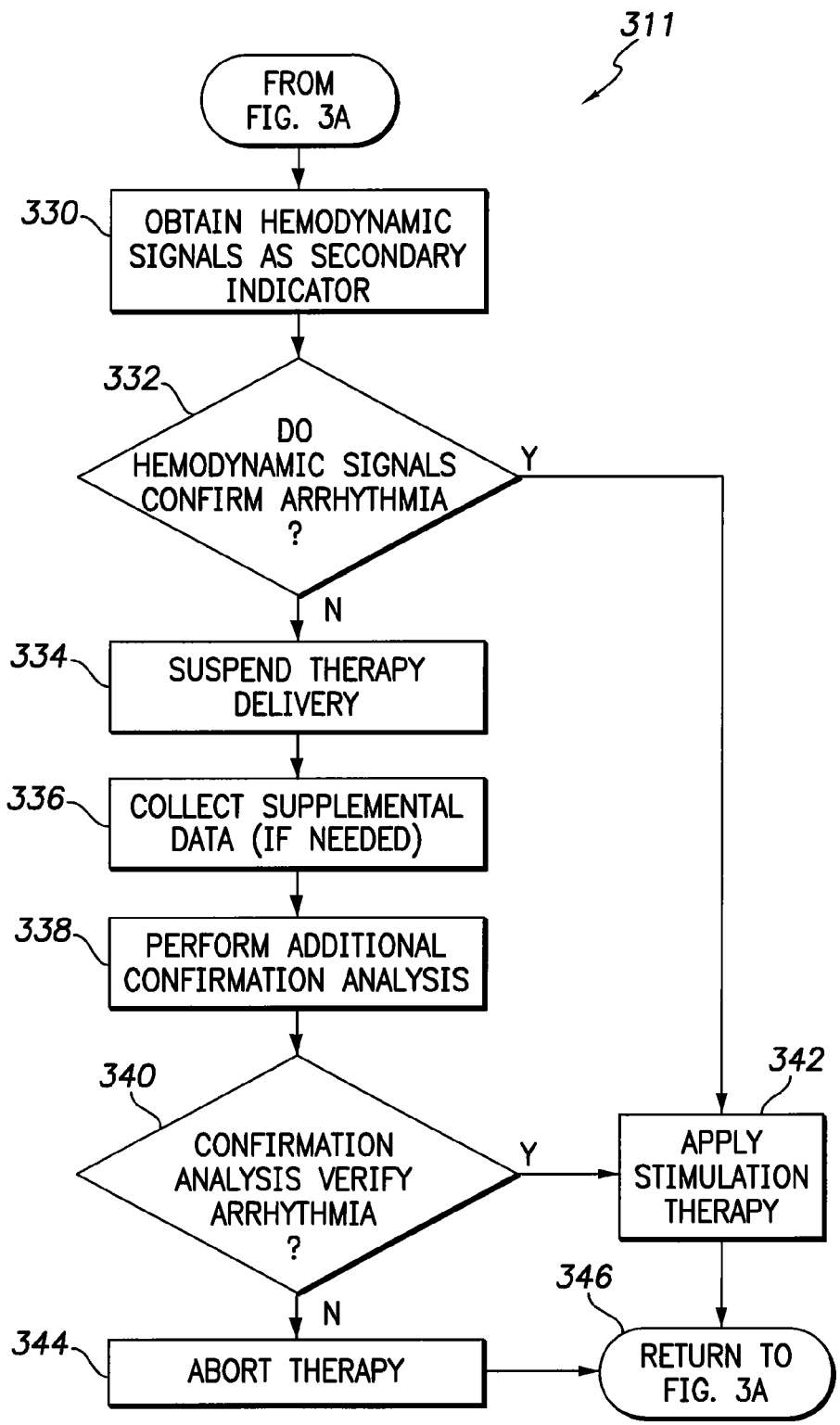

FIGS. 3A and 3B illustrate a process 300 for detecting potential lead failures of the IMD 100 (shown in FIG. 1). The process 300 operates to determine if a lead failure has occurred and, if a lead failure has occurred, to identify the electrode(s) associated with the lead failure. The process 300 may continue to operate, after a lead failure, is identified to determine if any additional lead failures occur. FIG. 4 is a table 400 in which each of the columns 402-408 includes information and data relevant to different types of lead states. Each column 404-408 corresponds to a different type or category of lead state, such as no fault, failure type 1, etc. The information in FIG. 4 will be referenced in connection with the following discussion of the process 300 in FIGS. 3A and 3B.

At 302, during the "no fault" operation of the lead 104 (shown in FIG. 1), cardiac signals are sensed over the bipolar or first channel and integrated bipolar or second channel. The first column 402 of the table 400 is associated with application of the process 300 when detecting a "no fault" condition of the IMD 100 (shown in FIG. 1), namely where no electrode failure is detected or identified in a lead. The first row 410 illustrates examples of different waveforms sensed by the first channel. The cell at the intersection of the first row 410 and the first column 402 illustrates an example of a normal physiologic bipolar waveform 430 sensed over the first or bipolar channel during the "no fault" operation of the lead 104. The bipolar waveform 430 in this embodiment represents the cardiac signals that are sensed using the RV tip electrode 122 and the RV ring electrode 124. The second row 412 illustrates examples of different waveforms sensed by the second channel. The cell at the intersection of the second row 412 and the first column 402 illustrates an example of a second or integrated bipolar waveform 436 that is sensed over the integrated bipolar channel during the "no fault" state of the lead 104. The bipolar and the integrated bipolar waveforms 430, 436 include, among other things, several R-waves 432 and S-waves 434 that are indicative of the normal physiologic behavior of the left ventricle. The third row 414 illustrates results that arise from the waveform combinations in 410 and 412.

In FIG. 3A, at 304, the cardiac signals sensed over the bipolar and integrated bipolar channels are compared to one another. In one embodiment, the cardiac rates of the cardiac signals are compared to one another. For example, the frequencies at which the R-waves 432 and/or the S-waves 434 occur over the bipolar and integrated bipolar channels may be compared. If the cardiac rates are similar to one another, then the similar cardiac rates may be indicative of a normally operating lead 104 (shown in FIG. 1) that does not exhibit signs or evidence of a potential lead failure. The cardiac rates may be considered similar to one another when the cardiac rates are within a predetermined threshold range of one another over a predetermined time period. For example, the cardiac rates may be determined to be similar if the cardiac rate sensed over the bipolar channel is within 10% of the cardiac rates sensed over the integrated bipolar channel during the previous 60 seconds or over a predetermined number of cardiac cycles. Alternatively, a different percentage range and/or time period may be used.

At 306, if the cardiac rates are found to be similar at 304, the cardiac rates sensed over the bipolar and integrated bipolar channels are compared to a predetermined rate threshold. The cardiac rates are compared to the predetermined rate threshold to determine if the cardiac rates are indicative of an abnormal heart rate, such as VT or VF. If the cardiac rates exceed the rate threshold, then the cardiac rates may be indicative of an abnormal heart rate. Alternatively, if the cardiac rates do not exceed the rate threshold or are not otherwise indicative of an abnormal heart rate, then the process 300 returns to 302. The process 300 may proceed in a loop-wise manner between 302, 304 and 306 where no potential lead failure is identified and the cardiac signals sensed over the bipolar and integrated bipolar channels do not exhibit cardiac rates that exceed the rate threshold.

If the cardiac rates are found to exceed the rate threshold at 306, flow moves to 308 where the cardiac signals are examined to determine if the signals correspond to physiologic (normal or abnormal) cardiac waveforms. For example, as shown in FIG. 4 at the cell at the intersection of row 416 and column 402, when a simultaneous or concurrent high rate is found in the cardiac signals sensed over the bipolar and integrated bipolar channels, a physiologic test may be performed on the cardiac signals. The signals may be examined to determine if the signal waveforms have characteristics similar to those of normal or abnormal physiologic cardiac waveforms. If the cardiac signal waveforms are similar to abnormal physiologic cardiac waveforms, then the high cardiac rate sensed over the bipolar and integrated bipolar channels may be due to "natural" causes, such as a cardiac condition, VT, VF, and the like. Alternatively, if the cardiac signal waveforms are not similar to normal or abnormal physiologic cardiac waveforms, then the high cardiac rate sensed over the bipolar and integrated bipolar channels may be due to an unnatural cause, such as chatter noise resulting from a fractured electrode and the like.

In one embodiment, the physiologic test at 308 involves analyzing values of one or more physiologic indicators or parameters of the cardiac signals sensed over the bipolar and integrated bipolar channels. The physiologic indicators may include the cardiac rates, a slew rate, a zero crossing rate, and an amplitude of the cardiac signal waveforms. The slew rate represents the slope or rate of change in the cardiac signal. The zero crossing rate represents the rate at which the cardiac signal switches between positive and negative voltage potentials. The values of the physiologic indicators may be compared to one another or to predetermined thresholds to determine if the signals are physiologic or non-physiologic. The predetermined thresholds are representative of physiologically acceptable limits for corresponding ones of the physiologic indicators.

Figure 5:
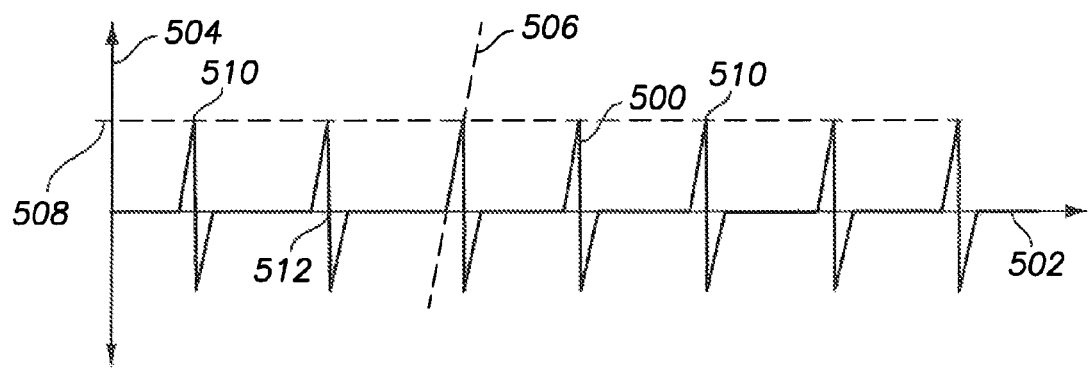
FIG. 5 illustrates examples of physiologic signal waveforms sensed over one or more of the bipolar and integrated bipolar channels in accordance with one embodiment.
Figure 6:
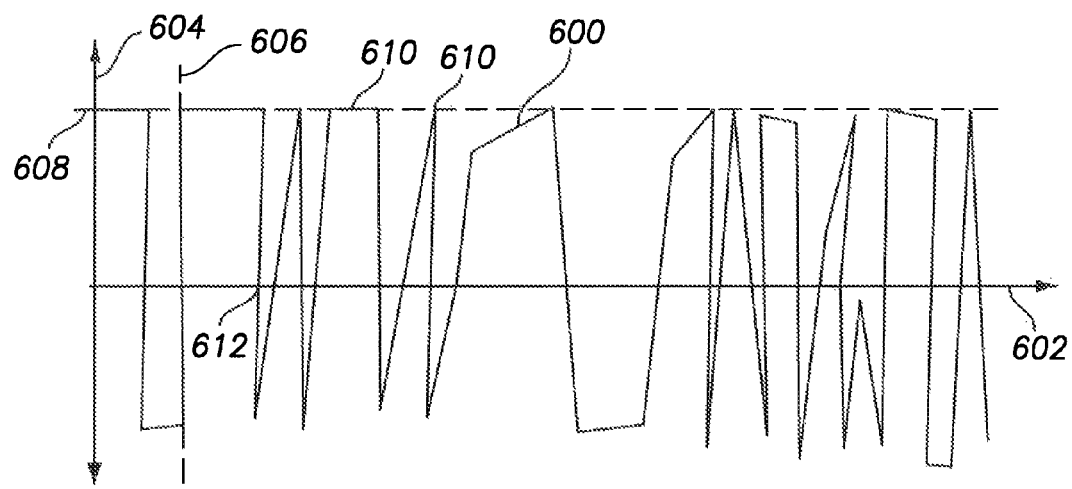
FIG. 6 illustrates examples of non-physiologic signal waveforms sensed over one or more of the bipolar and integrated bipolar channels in accordance with one embodiment.

FIG. 5 illustrates an example of a physiologic signal waveform 500 that may be sensed in accordance with one embodiment. FIG. 6 illustrates an example of a non-physiologic signal waveform 600 that may be sensed in accordance with one embodiment. The signal waveforms 500, 600 are shown alongside corresponding horizontal axes 502, 602 that are representative of time and vertical axes 504, 604 that are representative of the amplitude of the signal waveforms 500, 600.

The cardiac rate of the waveforms 500, 600 may be measured over a predetermined time period to determine if the waveforms 500, 600 are representative of physiologic waveforms. If the cardiac rates do not exceed a predetermined rate threshold, then the cardiac rates may indicate that the corresponding waveforms 500, 600 are physiologic. For example, if the time interval between consecutive ventricular contractions that is represented by each waveform 500, 600 does not exceed approximately 240 milliseconds, then the corresponding waveform 500, 600 may be physiologic (normal or abnormal). In another example, if the cardiac rate is approximately constant over the predetermined time period (such as the cardiac rate of the waveform 500), then the cardiac rate may indicate that the corresponding waveform is representative of a physiologic waveform. Alternatively, if the cardiac rate is not approximately constant over the time period (such as the cardiac rate of the waveform 600), then the cardiac rate may indicate that the corresponding waveform is not representative of a physiologic waveform. The cardiac rate may be considered at 308 to be approximately constant over a time period when the cardiac rate does not vary outside of a predetermined range or percentage during the time period. For example, the cardiac rate may be considered at 308 approximately constant if the cardiac rate does not vary by more than 10% during the time period.

Slew rates 506, 606 of the waveforms 500, 600 represent rates of change in the waveforms 500, 600. The slew rates 506, 606 may be referred to as the slope of the waveforms 500, 600. In one embodiment, the slew rate 506, 606 is the largest, or maximum, rate of change in the cardiac signals over the predetermined time period. For example, the slew rates of the waveform 500 may be approximately the same for the waveform 500 over the time period shown in FIG. 5. The slew rates of the waveform 600 varies during the time period shown in FIG. 6, with the largest slew rate 606 occurring during the approximately vertical portions of the waveform 600. The slew rates 506, 606 may be compared to one another and/or to a predetermined slew rate threshold to determine if the waveforms 500, 600 are physiologic waveforms. If the slew rate 606 is greater than the slew rate 506 (or exceeds the slew rate 506 by at least a predetermined threshold), then the slew rate 606 may be determined at 308 to indicate that the corresponding waveform 600 is non-physiologic. Alternatively, if the slew rate 606 exceeds a predetermined slew rate threshold then the slew rate 606 may be determined at 308 to indicate that the waveform 600 is non-physiologic.

Amplitudes 508, 608 of the waveforms 500, 600 represent a peak gain or strength 510, 610 of each waveform 500, 600. As shown in FIG. 5, the waveform 500 has approximately constant amplitudes 508 during the illustrated time period. While the waveform 600 may have approximately constant amplitudes 608, these amplitudes 608 may correspond to the maximum signal gain capability of the amplifiers 268 and 270. For example, the gain of signals sensed over a channel may be amplified by an amplifier such as the integrated bipolar amplifier 270 (shown in FIG. 2) or the bipolar amplifier 268 (shown in FIG. 2). However, the amplifiers 268, 270 have maximum capabilities gain that are reached when input signals have a substantial difference therebetween. These maximum capabilities may be referred to as the "rails" of the amplifiers 268, 270. If the output cardiac signals reach, or "hit", the rail of the amplifier 268, 270, then at 308, it is determined that the sensed signals may indicate that the corresponding channel is associated with a fractured lead or electrode.

Returning to FIG. 3A, at 308, the process 300 may examine the number of zero crossings 512, 612 occurring over a predetermined time period as a physiologic indicator. A zero crossing 512, 612 occurs each time that the corresponding waveform 500, 600 crosses over the time axis 502, 602. Alternatively, a zero crossing 512, 612 occurs each time the waveforms 500, 600 cross over the baseline (not shown) of the waveforms 500, 600. The baselines of the waveforms 500, 600 shown in FIGS. 5 and 6 are coextensive with the time axes 502, 602, but may be offset above or below the time axes 502, 602. The number or frequency of zero crossings 512, 612 may be indicative of the physiologic nature of the waveforms 500, 600. For example, the number and frequency of zero crossings 612 for the waveform 600 is greater than the number and frequency of zero crossings 512 for the waveform 500 over the same time period shown in FIGS. 5 and 6. The greater number of zero crossings 612 may be determined at 308 to indicate that the cardiac signals sensed over the corresponding channel may not be representative of cardiac behavior. Additionally, the frequency of zero crossings 612 may indicate that the waveform 600 is not representative of cardiac behavior and therefore is non-physiologic. For example, the frequency of zero crossings 612 may vary considerably relative to the frequency of zero crossings 512. The varying frequency of zero crossings 612 may indicate that the waveform 600 is not representative of cardiac behavior.

In addition or in another embodiment, the waveforms 500, 600 may be compared at 308 to one or more predetermined physiologic waveform templates to determine if the morphology, or shape, of the waveforms 500, 600 match or correspond to the waveform templates. The waveforms 500, 600 may be compared with the waveform templates to generate corresponding morphology indicators. If the morphology indicator for the waveform 500 is greater than the morphology indicator for the waveform 600, then the morphology indicators may indicate that the waveform 500 is physiologic and the waveform 600 is non-physiologic.

Returning to FIGS. 3A and 4, at 308, the waveforms 430, 436 that are sensed over the bipolar and integrated bipolar channels are found to be physiologic waveforms based on the analysis of one or more of the physiologic indicators discussed above (e.g., the cardiac rates, slew rates, amplitudes, morphology, and frequency or number of zero crossings). While the waveforms 430, 436 are physiologic, they are abnormal because the rate threshold was exceeded at 306. Next, in accordance with one embodiment, flow moves from 308 to 310. At 310, one or more stimulation pulses are applied to the heart 102 (shown in FIG. 1). For example, the waveforms 430, 436 are determined to have similar cardiac rates (at 304), to have cardiac rates that exceed a predetermined rate threshold (at 306) and to be physiologic waveforms (at 308), thereby indicating that the waveforms 430, 436 are not illustrative of a potential lead fracture, but do indicate tachycardia. As a result, no alert or notification of a potential lead failure is provided (as shown in the row 420) and no mitigating action is taken (as shown in the row 422). Because the waveforms 430, 436 indicate an abnormal heart rate such as VT or VF, the stimulation pulse is applied at 310 as a remedial course of action (as shown in the row 424). Once the stimulation pulse is applied, the process 300 may return to 302 to sense additional cardiac signals over the bipolar and integrated bipolar channels.

Returning to 308 in FIG. 3A, when the signals are determined to be physiologic, flow may move along an alternative path 309 instead of going directly to 310. When flow moves along 309, the process 300 suspends therapy (at least temporarily) until additional analysis can be performed at 311 to confirm or reject a potential arrhythmia. When an arrhythmia is confirmed at 311, a therapy is delivered. When a potential arrhythmia is rejected as false or negative, no therapy is delivered, and flow returns to 302.

FIG. 3B illustrates the process performed at 311 to confirm or reject a potential arrhythmia. At 330, the hemodynamic monitor module 267 obtains hemodynamic signals, such as from a memory buffer or from one or more of sensors 115, 117 and 119. The hemodynamic signals represent a secondary indicator of heart condition. At 332, the arrhythmia confirmation module 269 utilizes the secondary indicators (hemodynamic signals) to confirm or reject that the heart is experiencing an arrhythmia. As noted above, the hemodynamic indicator may represent an impedance plethysmothography measurement indicative of stroke volume, a pressure signal from a sensor located in a heart chamber, a heart sound signal, or a peak endocardial acceleration signal. The hemodynamic signals may be analyzed relative to templates or in connection with predetermined thresholds. Optionally, the hemodynamic signals may be analyzed relative to previously acquired hemodynamic signals from the same patient or a pool of patients. In the present example, the hemodynamic signals are obtained from the hemodynamic sensor after the first and/or second signals from the first and/or second channels are determined to be indicative of a potential lead failure. Optionally, hemodynamic signals may be continuously obtained throughout operation and not necessarily only after determination of a potential lead failure based on the first or second cardiac signals.

When the hemodynamic signals confirm an arrhythmia at 332, flow moves to 342 where a stimulation therapy is applied. When, at 332, the hemodynamic signals do not confirm an arrhythmia, but instead are indicative of normal sinus rhythm, flow moves to 334. When flow reaches 334, contradictory indicators have occurred, namely one or both of the first and second channels have indicated an arrhythmia, while the hemodynamic secondary indicators have indicated normal sinus rhythm. In this situation, it may not be necessary or desirable to immediately apply stimulation at 342. Instead, it may be desirable at 334 to, at least temporarily, suspend therapy delivery. Once the therapy is temporarily suspended, flow moves to 336 at which the hemodynamic monitor module 267 collects supplemental data (e.g., from memory buffer or from sensors 115, 117 and 119 if needed). Optionally, the operation at 336 may be entirely removed and flow may pass directly to 338 where the arrhythmia confirmation module 269 performs additional confirmation analysis seeking to confirm or reject the arrhythmia.

During the supplemental analysis time at 338, the arrhythmia confirmation module 269 performs confirmation analysis, such as by analyzing prior and/or new cardiac signals. Optionally, the confirmation analysis may analyze prior and/or new hemodynamic signals. The confirmation analysis may utilize more time consuming, robust algorithms for detecting arrhythmias that may not be readily usable in real time and continuously during normal operation of the IMD 100. The additional arrhythmia detection algorithms may be based solely upon analysis of pre-existing or new cardiac signals. The arrhythmia detection algorithms may be based solely upon pre-existing or new hemodynamic signals, or may be based on a combination of pre-existing and new cardiac and hemodynamic signals. The confirmation analysis may review cardiac and/or hemodynamic signals from other chambers of the heart (e.g., the left ventricle and left atrium) may collect and analyze new cardiac or hemodynamic signals and the like.

Once the confirmation analysis is complete at 338, it is determined at 340 whether the confirmation analysis has verified the arrhythmia or provided a negative result indicating that an arrhythmia does not exist. When the arrhythmia is verified, flow moves to 342 at which the stimulation therapy is now applied. When, at 340, the confirmation analysis provides a negative result indicating that no arrhythmia is present, flow moves to 344 at which the stimulation therapy is aborted or terminated entirely without being delivered. After 344 and 342, flow moves to 346 where the process returns to point B at the top of FIG. 3A.

Next, the process 300 will be described in connection with a first type of lead failure. In FIG. 4, the second column 404 of the table 400 represents identification of a first type of lead failure using the process 300. The first type of lead failure involves failure of an electrode that is used in only one of the first and second channels over which cardiac signals are sensed. For example, the first type of lead failure may be associated with the electrode used to sense cardiac signals on the integrated bipolar channel but not on the bipolar channel. As shown in rows 410, 412 when failure type 1 occurs, the bipolar channel senses physiologic waveform 438 while the integrated bipolar channel senses non-physiologic waveform 440 that does not have a physiologic shape. As described below, based at least in part of these waveforms 438, 440, the process 300 identifies the lead failure as a first type of lead failure.

At 302, the waveforms 438, 440 are sensed over the bipolar and integrated bipolar channels, as described above. At 304, the cardiac rates of the waveforms 438, 440 are compared with one another and are found to differ from one another. The difference in cardiac rates of the waveforms 438, 440 indicates that at least one of the cardiac signals represents a potential lead failure.

At 312, once the cardiac rates of the waveforms 438, 440 are found to differ, the memory addresses, to which the cardiac signals (and hemodynamic signals) are stored, may be temporarily blocked to prevent overwriting with additional new cardiac and hemodynamic signals. For example, the memory 236 (shown in FIG. 2) may include a memory buffer that stores a predetermined time period of cardiac signals recently obtained over the channels. Another buffer may store a time period of hemodynamic signals. The memory may be "frozen" and prevented from storing additional cardiac and hemodynamic signals in order to preserve the cardiac signals obtained during the previous predetermined time period. Optionally, the content of the cardiac signal memory buffer may be moved to another section of memory for longer term storage, thereby permitting the memory buffer to continue to store new cardiac signals. Also, hemodynamic signals in the memory buffer may be moved to longer term memory when waveforms 438, 440 are found to differ.

At 314, the frozen cardiac signals sensed by the integrated bipolar channel over the previous predetermined time period are obtained from the memory. The frozen cardiac signals sensed using the integrated bipolar channel are represented by the cardiac signal waveform 440. The waveform 440 is examined to determine if the waveform 440 is a physiologic or non-physiologic waveform. As described above, the cardiac signal waveform 440 may be classified as physiologic or non-physiologic by examining one or more physiologic indicators. The waveform 440 is found to have a non-physiologic waveform at 314. The non-physiologic shape of the waveform 440 may indicate that a potential lead failure has occurred and that the potential lead failure is associated with an electrode used to obtain the cardiac signals over the integrated bipolar channel.

Thus, flow moves to 316, where the frozen cardiac signals sensed by the bipolar channel over the previous predetermined time period are analyzed. The cardiac signals from the bipolar channel are examined to determine if the associated cardiac signal waveform 438 is a physiologic or non-physiologic waveform. As shown in column 404, the waveform 438 is a physiologic waveform.

Thus, flow moves to 318, where the process 300 declares the potential lead failure to be the first type of lead failure. If the waveform 438 of the bipolar channel is physiologic and the waveform 440 of the integrated bipolar channel is non-physiologic (as determined at 314), the waveforms 438, 440 may indicate that the potential lead failure is associated with an electrode that was used to obtain the non-physiologic waveforms 440, but that was not used to obtain the physiologic waveforms 438. In an embodiment where the bipolar channel is sensed using the RV tip electrode 122 and the RV ring electrode 124 and the integrated bipolar channel is sensed using the RV tip electrode 122 and the SVC coil electrode 128, the non-physiologic shape of the waveform 440 may indicate that the potential lead failure is caused by or associated with the SVC coil electrode 128.

As shown in rows 418-420, when a type 1 failure occurs, the process 300 may notify an operator of the IMD 100 (shown in FIG. 1) or physician of the existence of and the type of failure. For example, the IMD 100 may communicate with the external device 240 (shown in FIG. 2) to actuate an audible, visual and/or tactile alarm. The process also seeks to mitigate the identified lead failure. To do so, the lead coupled with the failed electrode may be replaced, as indicated in rows 422, 426. The process 300 may continue to apply bipolar pacing through the electrodes used to sense signals over the bipolar channel. The integrated bipolar channel may be disabled by the channel selection module 264 (shown in FIG. 2) to avoid sensing the erroneous signals using the electrode associated with the failure. Optionally, the channel selection module 264 may enable a new third channel for sensing that utilizes a different combination of electrodes to replace the disabled channel.

Optionally, at 318, it may obtain a secondary indicator from the electrode associated with the lead failure. For example, the process 300 verifies an identified lead failure by examining an electrical impedance characteristic of the electrode associated with the lead failure. Once the electrode is identified, the impedance measuring circuit 218 (shown in FIG. 2) measures the electrical impedance of the electrode. If the impedance exceeds a predetermined impedance threshold, then the impedance may represent a secondary indicator to indicate a fracture in the electrode. The secondary indication of an electrode fracture verifies the lead failure identified by the process 300.

Next at 319, it is determined whether the cardiac rate of the bipolar (first) channel signals exceeds a predetermined rate threshold. When the cardiac rate is below the rate threshold, then the process 300 may move to point B at the top of FIG. 3A and restart. When the cardiac rate exceeds the rate threshold, flow may move along path 315 to 311 where therapy is suspended until an additional confirmation analysis is performed to confirm or reject the arrhythmia as described above in connection with FIG. 3B.

Next, a second type of failure will be described. In FIG. 4, the third column 406 of the table 400 represents identification of a second type of lead failure using the process 300. Similar to the first type of lead failure, the second type involves failure of an electrode that is used in only one of the two channels over which cardiac signals are sensed. For example, the second type of lead failure may be associated with the electrode used to sense cardiac signals on the bipolar channel, but not on the integrated bipolar channel.

At 302, the waveforms 442, 444 are sensed over the bipolar and integrated bipolar channels, as described above. As shown in rows 410, 412, the second type of lead failure may result in the bipolar channel sensing a non-physiologic waveform 442, while the integrated bipolar channel senses a physiologic waveform 444. As described below, based at least in part on these sensed waveforms 442, 444, the process 300 identifies the lead failure as the second type of lead failure. To do so, at 304, the cardiac rates of the waveforms 442, 444 are compared with one another and are found to differ from one another. The difference in cardiac rates of the waveforms 442, 444 may indicate that at least one of the cardiac signals represents a potential lead failure. At 312, the memory is frozen to prevent storage of additional cardiac signals on the bipolar and integrated bipolar channels, as described above. At 314, the integrated bipolar cardiac signals are examined to determine if the signals (e.g., the waveform 444) indicate a physiologic waveform. The waveform 444 is found to have a physiologic waveform.

At 320, after the integrated bipolar channel signals are found to represent a physiologic waveform, the bipolar channel signals are examined to determine if the waveform 442 is a physiologic waveform. When the first channel signal is physiologic at 320, flow moves along path A to 306. When not physiologic at 320, flow moves to 322.

When both of the bipolar channel signals are found to be physiologic waveforms at 314 and 320, the cardiac rates of one or more of the bipolar channel signals and the integrated bipolar channels may be compared to a predetermined cardiac rate threshold at 306, as described above. If the cardiac rates are sufficiently high at 306, the process 300 may proceed through 308 to 310 where the stimulation pulse is applied. Otherwise, the process 300 may proceed back to 302.

Returning to 320, when the first channel is not physiologic, then at 322, the process 300 declares the lead failure to be the second type of lead failure. For example, as the bipolar channel signals represent a non-physiologic waveform while the integrated bipolar channel signals represent a physiologic waveform, the process 300 determines that an electrode used to obtain the bipolar channel signals but not to obtain the integrated bipolar channel signals is associated with the lead failure. In an embodiment where the bipolar channel obtains signals using the RV tip electrode 122 (shown in FIG. 1) and the RV ring electrode 124 (shown in FIG. 1) and the integrated bipolar channel obtains signals using the RV tip electrode 122 and the SVC coil electrode 128 (shown in FIG. 1), the process 300 declares the lead failure to be associated with the RV ring electrode 124. The process 300 may verify the second type of lead failure by measuring, at 322, a secondary electrode indicator such as an electrical impedance characteristic of the associated electrode, as described above.

As shown in rows 418-428 of FIG. 4, the process 300 at 322 may notify an operator of the IMD 100 (shown in FIG. 1) or a physician of the existence and type of the failure. The IMD 100 may mitigate the second type of lead failure by continuing to operate while ignoring the signals obtained by the electrodes associated with the bipolar channel. For example, the IMD 100 may disable sensing over the bipolar channel. The process 300 may remedy the lead failure at least in part by directing the IMD 100 to switch from bipolar pacing to integrated bipolar pacing of the heart 102 (shown in FIG. 1). For example, the process 300 may direct the IMD 100 to refrain from using the RV tip electrode 122 and RV ring electrode 124 to pace the heart 102 and instead use the RV tip electrode 122 and the SVC coil electrode 128 to pace the heart 102.

After 322, it is determined at 323 whether the signal over the second channel has a rate that exceeds a rate threshold. If not, flow returns to the start at B. If the second channel has a signal rate that exceeds the rate threshold, flow moves to 311 where therapy is suspended at least temporarily as discussed above.

Next, the third type of failure is discussed. In FIG. 4, the fourth column 408 of the table 400 represents identification of a third type of lead failure using the process 300. In contrast to the first and second types of lead failure, the third type involves the failing electrode and is common to two or more of the channels over which cardiac signals are sensed. For example, the third type of lead failure may be associated with the electrode used to sense cardiac signals on the bipolar and integrated bipolar channels.

At 302, the waveforms 446, 448 are sensed over the bipolar and integrated bipolar channels, as described above. As shown in the rows 410, 412, both the bipolar and integrated bipolar channels sense non-physiologic waveforms 446, 448. At 304, the cardiac rates of the waveforms 446, 448 are compared with one another and are found to differ from one another. The difference in rates of the waveforms 446, 448 may indicate that at least one of the cardiac signals represents a potential lead failure. At 312, the memory is frozen and prevented from storing additional hemodynamic and cardiac signals. At 314, the integrated bipolar cardiac signals are examined to determine if the signals (e.g., the waveform 448) represent a physiologic waveform. In the embodiment represented by the column 408, the waveform 448 is found to have a non-physiologic waveform. At 316, after the integrated bipolar channel signals are found to be non-physiologic (at 314), the bipolar channel signals are examined to determine if the signals (e.g., the waveform 446) are physiologic. In the embodiment represented by the column 408, the waveform 446 is found to have a non-physiologic waveform.

At 324, after the bipolar and integrated bipolar channel signals are determined to be non-physiologic at 314 and 316, the bipolar and integrated bipolar channel signals are compared to determine if the signals are correlated with one another. For example, the signals may be compared to determine if the signals approximately match one another over a predetermined time period. One or more of the physiologic indicators described above may be used to determine if the bipolar and integrated bipolar channel signals are correlated with one another. If at least a predetermined number of the physiologic indicators for each of the bipolar and integrated bipolar channels are within a predetermined range or variance of one another, then the bipolar and integrated bipolar channel signals may be correlated with one another. In the embodiment shown in the fourth column 408, the bipolar and integrated bipolar channel signals shown in the rows 410, 412 are found to be correlated with one another.

At 324, when the signals from the bipolar and integrated bipolar channels are not correlated with one another, the signals may not indicate that the potential lead failure is the third type of lead failure. Instead, the signals may indicate a different type of lead failure or that no lead failure has occurred. As a result, the process 300 may return to 302 where additional signals are obtained over the channels to determine if a potential lead failure exists or if the IMD 100 (shown in FIG. 1) is operating in the "no fault" category described in column 402 of the table 400 and described above.

At 324, when the bipolar and integrated bipolar channel signals are found to be correlated with one another, at 326, the process 300 identifies the potential lead failure as the third type of failure. For example, when both of the bipolar and integrated bipolar signals are found to be non-physiologic and correlated with one another, the electrode that is common to both the bipolar and integrated bipolar channels is identified as associated with the lead failure. In an embodiment where the RV tip electrode 122 (shown in FIG. 1) is used to sense cardiac signals on both the bipolar and integrated bipolar channels, the RV tip electrode 122 is associated with the lead failure. The process 300 may verify the lead failure by measuring an electrical impedance characteristic of the associated electrode, as described above.

An operator or physician may be notified of the existence and type of third type of lead failure. As shown in row 422 of the table 400, the third type of lead failure may be mitigated by disabling the channels associated with the failed electrode. For example, the IMD 100 (shown in FIG. 1) may ignore cardiac signals obtained over both the bipolar and integrated bipolar channels. As the electrode associated with the lead failure is used to obtain signals over both channels, the signals obtained over both channels are affected by the failed electrode. In order to avoid pacing or applying stimulation pulses based on signals obtained over a failed lead, both channels are ignored. The IMD 100 may avoid pacing the heart 102 (shown in FIG. 1) or applying stimulation pulses to the heart 102, even if the cardiac rates of the signals obtained over the channels indicate a sufficiently high rate such that a stimulation pulse would otherwise be applied. As shown in row 426, the lead 104-108 (shown in FIG. 1) having the electrode associated with the lead failure may be replaced in order to remedy the lead failure. Alternatively, the IMD 100 may be reconfigured to use different combinations of electrodes to sense cardiac signals over a different channel. For example, if the RV tip electrode 122 (shown in FIG. 1) is declared to be the electrode associated with the lead failure, the IMD 100 may switch to sensing cardiac signals over a third channel different from the bipolar and integrated bipolar channels. The third channel may be sensed using the RV ring electrode 124 (shown in FIG. 1) and the SVC coil electrode 128 (shown in FIG. 1), or another combination of electrodes coupled with the failed lead or with another lead.

After 326, flow moves to 311, where hemodynamic signals are collected and analyzed to confirm or reject arrhythmias as discussed in connection with FIG. 3B.

Figure 7:
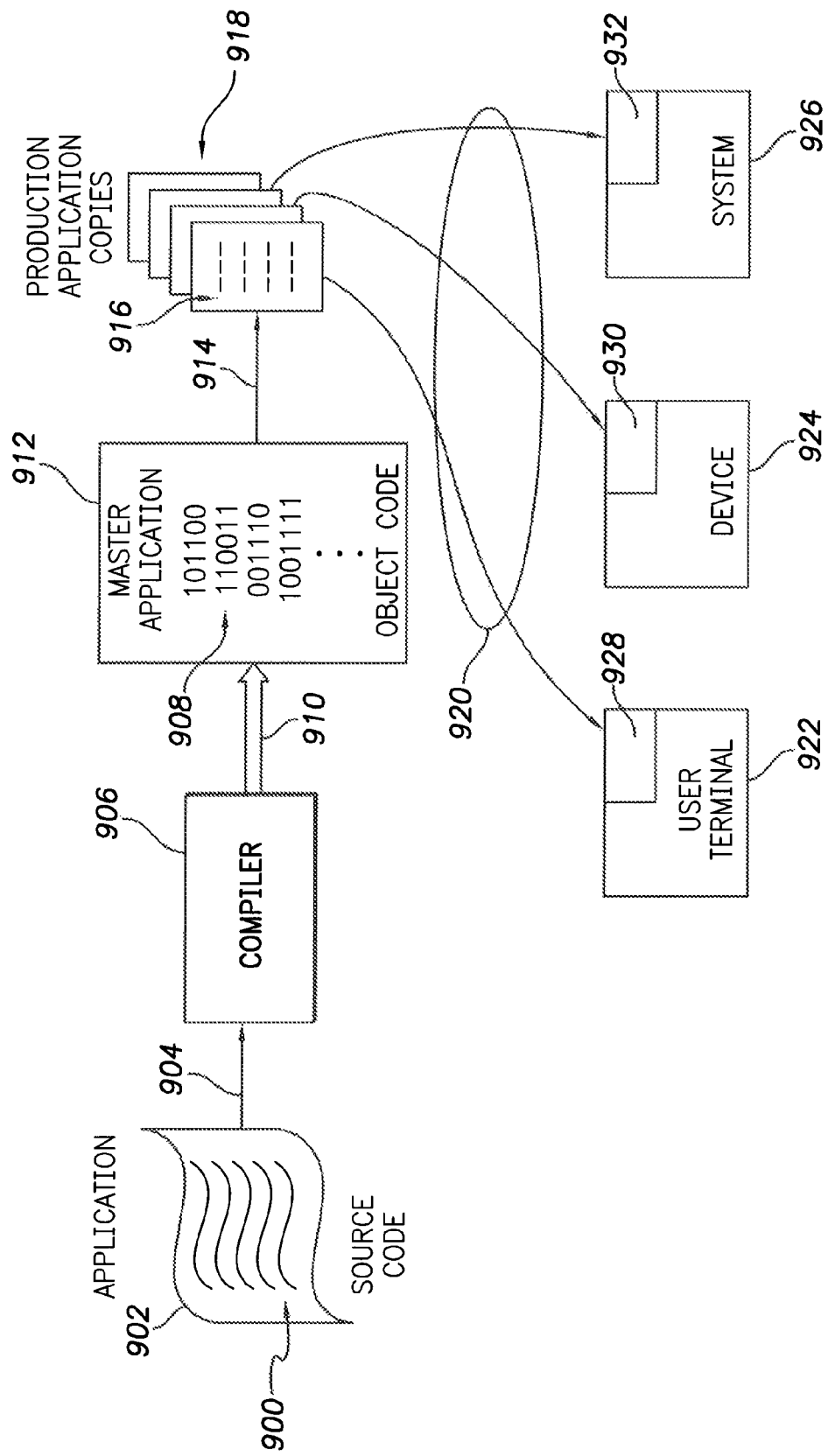
FIG. 7 illustrates a block diagram of exemplary manners in which embodiments of the present invention may be stored, distributed, and installed on a computer-readable medium.

In one embodiment, the third type of lead failure may be detected by the process 300 in a different manner. As described above in connection with the "no fault" operation of the IMD 100 (shown in FIG. 1), at 308, the signals obtained over the bipolar and integrated bipolar channels are examined to determine if the signals have physiologic waveforms. If the waveforms do not have physiologic waveforms, the signals may indicate the third type of lead failure. For example, while the signals may have similar cardiac rates (determined at 304) and the cardiac rates exceed a rate threshold (determined at 306), the signals on both channels may be based on a lead failure involving an electrode common to both channels. In order to check for the third type of lead failure, at 324, the signals are compared to determine if the signals are correlated as described above. Based on this additional check, the process 300 may declare that the signals are based on the third type of lead failure. For example, the third type of lead failure may be identified when both the bipolar and integrated bipolar channel signals are non-physiologic and correlated with one another FIG. 7 illustrates a block diagram of exemplary manners in which embodiments of the present invention may be stored, distributed, and installed on a computer-readable medium. In FIG. 7, the "application" represents one or more of the methods and process operations discussed above. The application is initially generated and stored as source code 900 on a source computer-readable medium 902. The source code 900 is then conveyed over path 904 and processed by a compiler 906 to produce object code 908. The object code 908 is conveyed over path 910 and saved as one or more application masters on a master computer-readable medium 912. The object code 908 is then copied numerous times, as denoted by path 914, to produce production application copies 916 that are saved on separate production computer-readable medium 918. The production computer-readable medium 918 is then conveyed, as denoted by path 920, to various systems, devices, terminals and the like. A user terminal 922, a device 924 and a system 926 are shown as examples of hardware components, on which the production computer-readable medium 918 are installed as applications (as denoted by 928 through 932). For example, the production computer-readable medium 918 may be installed on the IMD 100 (shown in FIG. 1) and/or the microcontroller 216 (shown in FIG. 2). Examples of the source, master, and production computer-readable medium 902, 912, and 918 include, but are not limited to, CDROM, RAM, ROM, Flash memory, RAID drives, memory on a computer system, and the like. Examples of the paths 904, 910, 914, and 920 include, but are not limited to, network paths, the internet, Bluetooth, GSM, infrared wireless LANs, HIPERLAN, 3G, satellite, and the like. The paths 904, 910, 914, and 920 may also represent public or private carrier services that transport one or more physical copies of the source, master, or production computer-readable medium 902, 912 or 918 between two geographic locations. The paths 904, 910, 914 and 920 may represent threads carried out by one or more processors in parallel. For example, one computer may hold the source code 900, compiler 906 and object code 908. Multiple computers may operate in parallel to produce the production application copies 916. The paths 904, 910, 914, and 920 may be intra-state, inter-state, intra-country, inter-country, intra-continental, inter-continental, and the like.

The operations noted in FIG. 7 may be performed in a widely distributed manner world-wide with only a portion thereof being performed in the United States. For example, the application source code 900 may be written in the United States and saved on a source computer-readable medium 902 in the United States, but transported to another country (corresponding to path 904) before compiling, copying and installation. Alternatively, the application source code 900 may be written in or outside of the United States, compiled at a compiler 906 located in the United States and saved on a master computer-readable medium 912 in the United States, but the object code 908 transported to another country (corresponding to path 914) before copying and installation. Alternatively, the application source code 900 and object code 908 may be produced in or outside of the United States, but production application copies 916 produced in or conveyed to the United States (for example, as part of a staging operation) before the production application copies 916 are installed on user terminals 922, devices 924, and/or systems 926 located in or outside the United States as applications 928 through 932. As used throughout the specification and claims, the phrases "computer-readable medium" and "instructions configured to" shall refer to any one or all of (i) the source computer-readable medium 902 and source code 900, (ii) the master computer-readable medium and object code 908, (iii) the production computer-readable medium 918 and production application copies 916 and/or (iv) the applications 928 through 932 saved in memory in the terminal 922, device 924, and system 926.

It is to be understood that the above description is intended to be illustrative, and not restrictive. For example, the above-described embodiments (and/or aspects thereof may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting potential failures by an implantable medical lead, comprising:
    sensing a first signal over a first channel between a first combination of electrodes on the lead;
    sensing a second signal from a second channel between a second combination of electrodes on the lead;
    comparing a first cardiac rate of the first signal to a second cardiac rate of the second signal;
    determining if the first and second signals are physiologic if the first cardiac rate is approximately equal to the second cardiac rate;
    determining whether at least one of the first and second signals is representative of a potential failure in the lead as a function of the rate comparison and the physiologic determination; and
    identifying a failure and the electrode associated with the failure based on which of the first and second sensed signals is representative of the potential failure.

2. The method of claim 1, further comprising:
    when the first and second sensed signals are both representative of the potential failure, determining whether the first and second sensed signals are correlated with one another; and
    when the first and second sensed signals are correlated, declaring an electrode common to both of the first and second combinations to be associated with the failure.

3. The method of claim 1, further comprising changing at least one of a pacing configuration and a pacer sensing configuration based on the electrode associated with the failure.

4. The method of claim 1, further comprising comparing at least one of amplitude, rate and slew rate of the first and second sensed signals to a predetermined threshold representative of a physiologically acceptable limit for the corresponding one of amplitude, rate and slew rate.

5. The method of claim 1, further comprising disabling sensing over at least one of the first and second channels that is associated with the failure, and enabling a different third channel to sense signals from a third combination of electrodes.

6. The method of claim 1, further comprising notifying a physician of existence of the failure and of the type of failure.

7. The method of claim 1, wherein the first combination of electrodes includes a ring electrode and a tip electrode and the second combination of electrodes includes a coil electrode and the tip electrode.

8. The method of claim 1, further comprising declaring a failure of an electrode of the first combination of electrodes when the first signal is representative of a non-physiologic signal and the second signal is representative of a physiologic signal.

9. The method of claim 1, further comprising declaring a failure of an electrode common to both the first and second combinations of electrodes when the first and second signals are both representative of non-physiologic signals.

10. A method for detecting potential failures by an implantable medical lead, comprising:
    sensing a first signal over a first channel between a first combination of electrodes on the lead;
    determining whether the first signal is representative of a potential failure in the lead;
    obtaining a secondary indicator of heart condition; and
    utilizing the secondary indicator to confirm an arrhythmia of the heart when the determining operation identifies the lead to include the potential failure.

11. The method according to claim 10, wherein the secondary indicator represents a hemodynamic indicator from one of an impedance plethysmography measurement indicative of stroke volume in the heart, a pressure sensor located in a heart chamber, a heart sound sensor and a peak endocardial acceleration sensor.

12. The method according to claim 10, wherein the secondary indicator is obtained from a hemodynamic sensor, the secondary indicator being tested after the determining operation identifies the potential failure based on the first signal, the secondary indicator being analyzed before delivery of a therapy.

13. The method according to claim 10, wherein the secondary indicator is obtained from a hemodynamic sensor, the method further comprising performing additional analysis of a heart, when the secondary indicator is representative of normal sinus rhythm, before delivering a therapy.

* * * * *